United States Patent [19]

Herold et al.

[11] Patent Number: 5,080,262

[45] Date of Patent: Jan. 14, 1992

[54] MIXING DISPENSER FOR PASTY MASSES

[75] Inventors: Wolf-Dietrich Herold, Seefeld; Gerd Brandhorst, Munich; Günter Rehfeld, Diessen, all of Fed. Rep. of Germany

[73] Assignee: THERA Patent GmbH & Co. KG Gesellschaft fur industrielle Schutzrechte, Seefeld, Fed. Rep. of Germany

[21] Appl. No.: 465,366

[22] Filed: Jan. 16, 1990

[30] Foreign Application Priority Data

Jan. 17, 1989 [DE] Fed. Rep. of Germany ... 8900469[U]

[51] Int. Cl.⁵ .............................................. B67D 5/52
[52] U.S. Cl. ..................... 222/135; 222/137; 222/145; 222/459; 422/135; 422/225; 422/229
[58] Field of Search ............. 422/131, 133, 135, 224, 422/225, 229; 366/338, 339; 222/137, 145, 326, 327, 459, 135

[56] References Cited

U.S. PATENT DOCUMENTS

| | | |
|---|---|---|
| 3,575,319 | 4/1971 | Safianoff ................... 222/459 |
| 3,767,085 | 10/1973 | Cannon et al. ............. 222/137 |
| 4,014,463 | 3/1977 | Hermann . |
| 4,366,919 | 1/1983 | Anderson ................... 222/137 |
| 4,432,469 | 2/1984 | Elbe et al. .................. 222/137 |
| 4,538,920 | 9/1985 | Drake ........................ 222/137 |
| 4,690,306 | 1/1987 | Stäheli ....................... 222/137 |
| 4,767,026 | 8/1988 | Keller et al. ............... 366/339 |
| 4,846,373 | 7/1989 | Penn et al. ................. 366/339 |
| 4,890,771 | 1/1990 | Morel et al. ............... 222/137 |

FOREIGN PATENT DOCUMENTS 2501080 9/1982 France ...................... 222/137

Primary Examiner—Peter Kratz
Attorney, Agent, or Firm—Foley & Lardner

[57] ABSTRACT

A device for mixing and dispensing pasty masses comprises a container 10 having two parallel compartments 12, 13 for accommodating two components which react with each other and an opening 14 including two concentric spaces 15, 18 each communicating with a respective one of the compartments 12, 13. A static mixer 11 is screwed onto the container opening 14 and includes a sleeve-like separator 24 at its entrance end. In the assembled state, the separator 14 is sealingly contiguous with a cylindrical partition 16 which separates the two spaces 15, 18 of the container opening 14 from each other. The location where the two components are combined is thus axially spaced from the location where the component strings are interrupted upon removal of the mixer 11, so that clogging of the container 10 caused by mutual carry-over of the components is prevented.

9 Claims, 3 Drawing Sheets

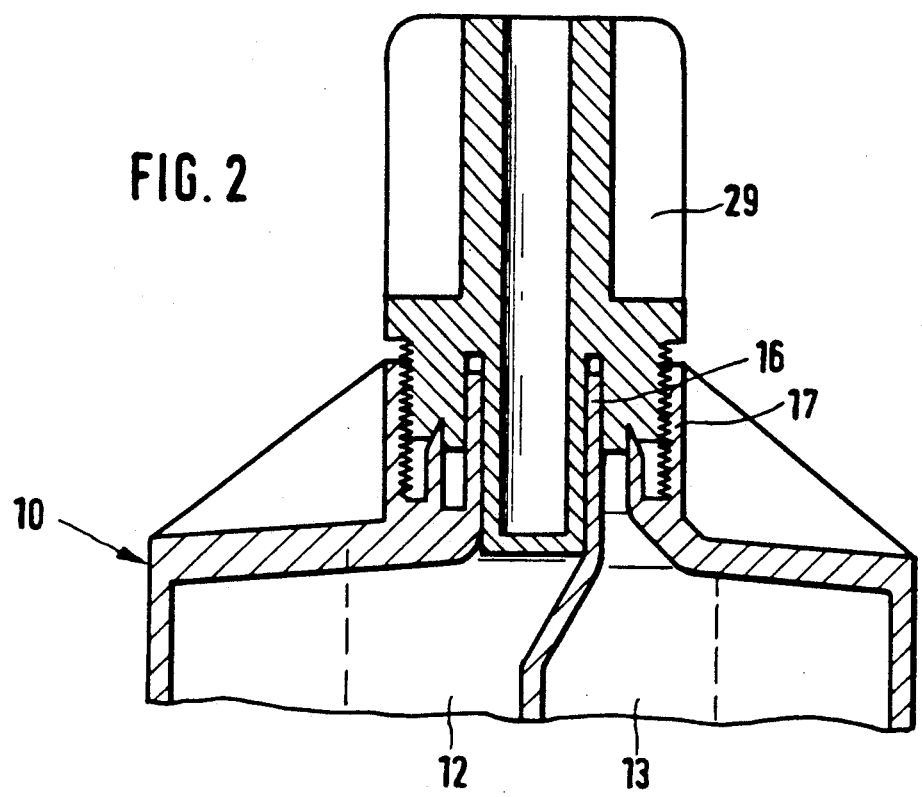
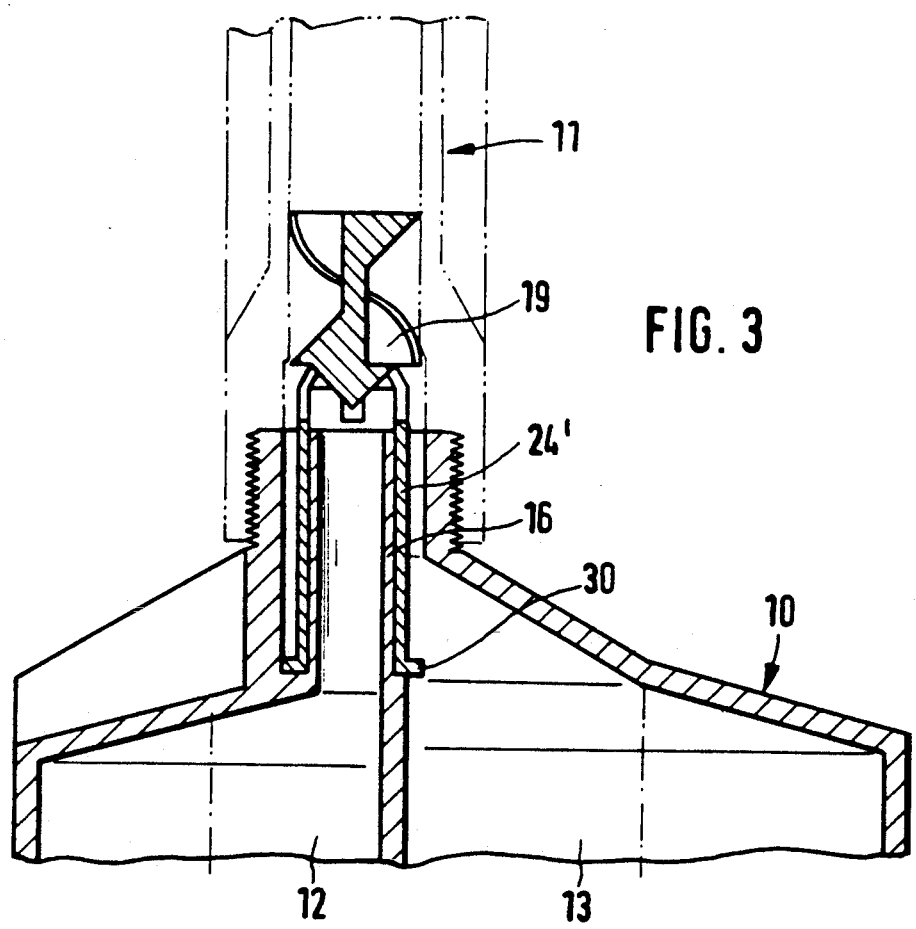

MIXING DISPENSER FOR PASTY MASSES

BACKGROUND OF THE INVENTION

This invention relates to device for mixing two components which react with each other and for dispensing the pasty mass mixed therefrom.

U.S. Pat. No. 4,014,463 discloses a device for mixing and dispensing pasty masses in which two components, that are to be blended to from the desired mass, are contained in two compartments of a container. The compartments are disposed axially in series, the rearward compartment being movable like a piston relative to the forward compartment. The component contained in the rearward compartment will flow through a tube axially passing through the forward compartment to exit at the forward end thereof, while the material contained in the forward compartment exits into the annular space defined between the tube and the outer wall of the container opening.

The concentrically extruded material is urged through a static mixer which is adapted to be inserted into the container opening and in which the two components are mixed to form a homogenous pasty mass to be dispensed from the front discharge end of the mixer.

The static mixer is composed in the usual way from a plurality of blade members which are arranged serially with alternating senses of rotation in the discharge direction, the leading edge of each downstream blade member extending normal to the trailing edge of the preceding upstream blade member.

Such devices with static mixers are used particularly in cases where it is important thoroughly to blend two components with each other so as to obtain a pasty mass exhibiting homogeneous properties such as a dental impression compound or a two-component adhesive.

In the known device, the annular area of the container opening has a flexible sealing disk provided therein which is to be opened by the discharge pressure of the respective component while it is to be closed when the pressure is relieved. This is intended to prevent inadvertent mixing of the two components when the dispensing operation is interrupted. Mixing will merely take place in the area outside of the sealing disk and in the static mixer.

Prior to the renewed use of the device the mixer is withdrawn from the container opening and discarded together with the hardened mass left therein, and any residues of the partially mixed and hardened mass are removed from the area of the container opening outside the sealing disk. The mixer is connected to the container by means of a clamping nut which surrounds the mixer casing and is threaded onto the front end of the container.

In the known device, the described sealing disk poses a problem because, on the one hand, it should be as compliant as possible to permit sufficient widening of its central opening surrounding the tube while, on the other hand, it should exhibit sufficiently high restoring forces to seal the opening in the absence of a discharge pressure. In practical use, such a sealing disk will result in an undesired increase of the required discharge pressure.

It is a further drawback of the known device that, after removal of a previously used mixer and prior to renewed use, the remaining hardened mass has to be removed manually from the opening area of the container. This cleaning operation is particularly difficult in the relatively narrow opening area of the internal dispensing tube and can hardly be performed completely. However, any cross-sectional reduction caused by non-removed residues will, upon renewed use, not only lead to a change in the mixing ratio and thus to a deterioration of the properties of the finished mass but also result in an increase in pressure. With certain masses it may even lead to clogging, thereby rendering the entire device inoperative.

Finally, the known device requires a specially configured container which in turn requires considerable efforts in respect of manufacture, filling and assembly. Commonly available filling machines cannot readily be used for filling the known device.

SUMMARY OF THE INVENTION

It is an object of the present invention to provide a device for mixing and dispensing pasty masses, which ensures thorough mixing of the components and easy handling, and in which clogging in the non-used state due to inadvertent carry-over of the components is prevented.

The object is met by a device for mixing two components which react with each other and for dispensing the pasty mass mixed therefrom which comprises a body member having separate feed means for the components, a circular opening having a partition dividing the opening into an inner space and an annular outer space, the inner space communicating with one of the feed means, and the outer space communicating with another one of the feed means; a static mixer including a tubular housing having a rear open end adapted for connection to the opening of the body member, and a dispensing opening at its forward end; and a sleeve-like separating element (24) joined to the rear end of the mixer, the separating element, upon fitting of the mixer onto the body member, being sealingly connected to the cylindrical partition to constitute an extension thereof.

In the device according to the invention, the sleeve-like separating element, which in operation is sealingly contiguous with the partition, will cause the two components to contact each other only at the point of entry of the mixer and will cause this area to be removed jointly with the separating element when the mixer is removed from the body member. The separating element thus ensures that the mixing location and the location where the components streams are interrupted when the mixer is removed are spaced from each other.

In an embodiment of the invention, the separating element is formed with outer and inner peripheral walls defining a rearwardly open annular groove for receiving the partition. The locations where the component strings issuing from their compartments are interrupted are thus displaced relative to the front end of the partition, so that a considerable distance from the mixing location is achieved and any carry-over in the area of the opening is avoided even more safely. When the annular groove formed within the separating element is pushed onto the partition provided in the container opening, any still remaining residues will be wiped off.

It is further advantageous for the mixer to comprise a cylindrical housing having a threaded portion of the body member defining the circular opening. The additional nut required in the prior art device can thus be omitted. Also, such a direct engagement results in a safe and tight joint between the mixer and the container, which is highly desirable in view of the high pressures necessary for dispensing high-viscosity masses. Also, when the body member is detached from the mixer by unscrewing, this action has both a breaking and a shearing effect on the two component strings.

For economic reasons, the external threads that are less expensive to make are preferably provided on the mixer which is discarded after use.

As a further advantageous measure, the end face of the externally threaded housing portion and the end face of the outer peripheral wall lie substantially in the same plane. A well defined shearing surface is thereby obtained also in the annular space of the body opening.

When the ratio of the lengths of the outer and inner peripheral walls is made to be substantially inversely proportional to the ratio of the cross-sectional areas of the outer and inner spaces of the circular opening, it becomes possible to interrupt both component strings in such a manner that, upon re-use of the device with a fresh mixer fitted onto the container, these strings will simultaneously arrive at the entry of the mixer so that the desired mixing ratio is immediately obtained.

According to another preferred embodiment, the separating element externally engages the cylindrical partition and an outwardly facing annular flange is provided at the end of the separating element. This is a simple way of placing the point of breakage of the component string passing through the annular space at a location which is displaced rearwardly from the front end of the opening.

In a further advantageous embodiment, the feed means are disposed in side-by-side relationship with axes parallel to the dispensing direction, and the mixer includes a series of blades, the leading edge of the first mixer blade lying in the plane defined by the axes. The compartments are thus disposed in side-by-side relationship as is common with conventional filling machines. Due to the orientation of the first mixer blade, asymmetrical introduction of the component into the annular space of the opening will not impair the homogeneity of the mixed product.

The separating element may be formed integrally with the mixer to achieve a configuration which is composed of a minimum number of parts and thus convenient to handle.

The body member may be formed as a container having compartments for holding the components to be mixed, the compartments constituting the feed means and being sealed by pistons. Alternatively, the body member may be composed of structural parts adapted to be mounted in a working table, with the feed means being formed by supply lines for connection to separate external component reservoirs.

BRIEF DESCRIPTION OF THE DRAWINGS

FIG. 2 shows part of the device illustrated in FIG. 1, with the mixer being replaced by a closure plug.

FIGS. 3 and 4 each show part of a mixing dispenser according to alternative embodiments.

DETAILED DESCRIPTION OF PREFERRED EMBODIMENTS

Figure 1:
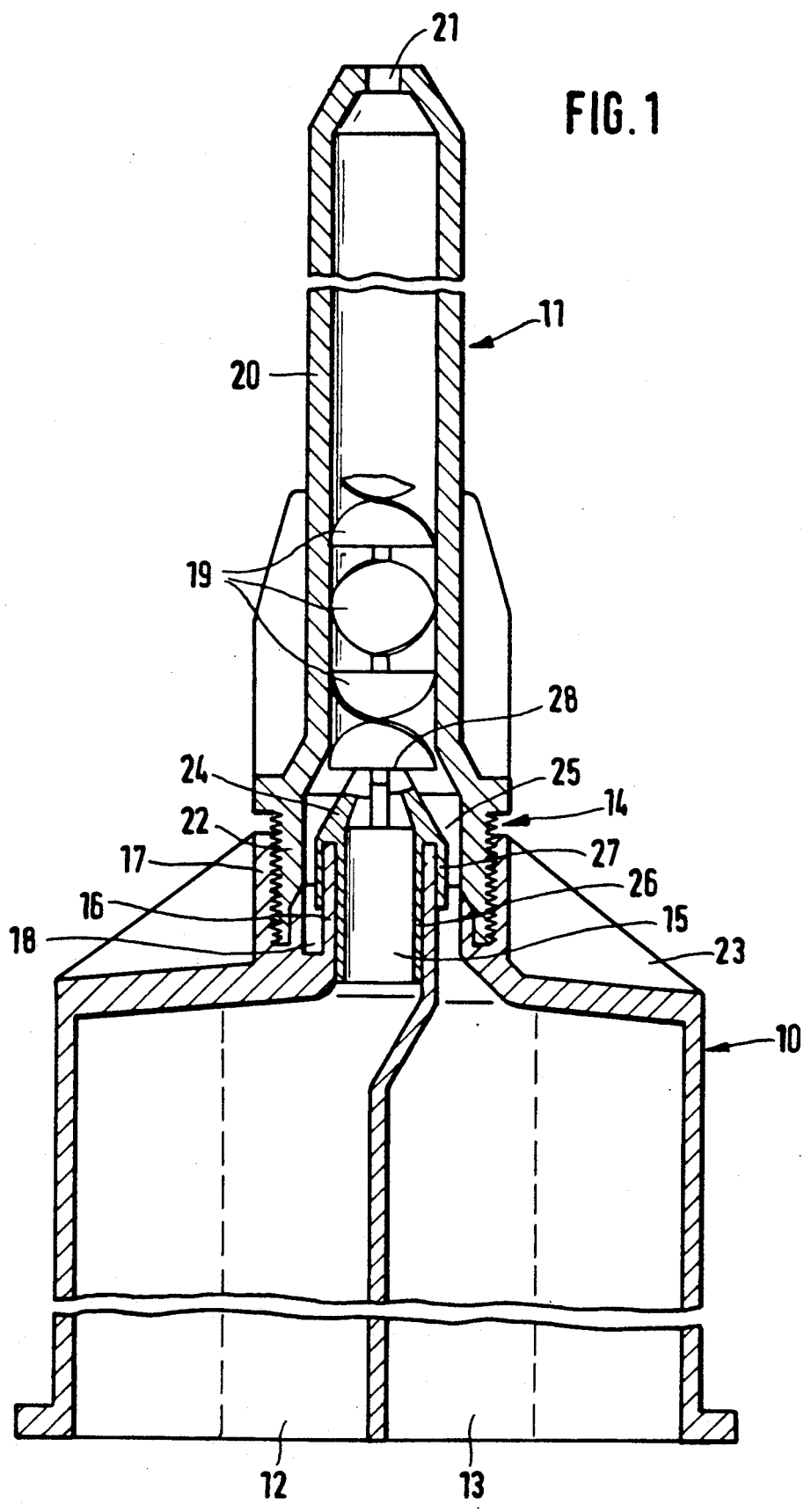
FIG. 1 is a longitudinal sectional view of a mixing dispenser according to one embodiment of the invention.

As shown in FIG. 1, the device comprises a container 10 and a static mixer 11. The container 10 includes two compartments 12 and 13 having cylindrical interior spaces and parallel axes. In the vicinity of the container opening 14, the compartment 12 opens to an inner space 15 of circular cross-section defined by a cylindrical partition 16. The compartment 13 opens into an outer annular space 18 formed between the cylindrical partition 16 and a concentric outer peripheral wall 17 of the opening 14.

The compartments 12 and 13 are used to accomodate two components of the pasty mass to be produced, which components react chemically with each other. At their rear ends, which are shown open in FIG. 1, the compartments 12 and 13 are closed by pistons (not illustrated) actuated by a common advancing mechanism (also not illustrated) for simultaneously dispensing both components.

The mixer 11 comprises a series of mixer blades 19 formed integrally with short intermediate axial portions. The mixer blades 19 are disposed along the mixer axis, each blade being configured somewhat like part of a helix having a length corresponding to one-half turn. The blades 19 are arranged with alternating turning senses, the leading edge of each mixer blade 19 extending normal to the traling edge of the respective preceding blade.

The mixer blade assembly is fitted without clearance in a barrel 20 the rear open end (the lower end in FIG. 1) of which is adapted to be connected to the opening 14 of the container 10 and the front end (the upper end in FIG. 1) is provided with a dispensing opening 21 for the mixed pasty mass. The lower barrel end is provided with a sleeve 22 having an outer diameter which corresponds to the inner diameter of the container-near part of the peripheral wall 17.

The outer surface of the sleeve 22 is provided with screw threads for engagement with internal threads formed in the enlarged portion of the peripheral wall 17 remote from the barrel. To improve the sealing between the container 10 and the barrel 20, the abutting faces of the peripheral wall 17 and the sleeve 22 have complementary conical shapes. Fins 23 integrally formed with the outside of the barrel 20 facilitate handling of the mixer 11 when it is screwed into the container opening 14.

At the entrance end of the mixer blade assembly there is disposed a separating element 24 integrally formed with the first mixer blade 19 and having a sleeve-like overall design with two open ends. The separating element 24 is provided with a rearwardly facing annular groove 25 for receiving the cylindrical partition 16 of the container 10. The annular groove 25 is defined by an internal cylindrical peripheral wall 26 and a coaxial external cylindrical peripheral wall 27 and is dimensioned so that the peripheral walls 26 and 27 sealingly enclose the partition 16.

The axial length of the outer peripheral wall 27 corresponds approximately to the axial length of the sleeve 22 constituting the end of the barrel 20, so that the peripheral wall 27 and the sleeve 22 terminate substantially in the same plane normal to the dispensing direction. The internal peripheral wall 26 of the separating element 24, on the other hand, extends farther into the container. The ratio of the axial length of the external peripheral wall 27 to that of the internal peripheral wall 26 is substantially inversely proportional to the ratio of the cross-sectional area of the annular space 18 so that of the inner space 15.

In use of the device, the two components contained in the compartments 12 and 13 are fed, by the simultaneous advance of the two pistons (not illustrated), into the mixer 11 at a ratio defined by the cross-sectional areas of the compartments 12 and 13 and enter the mixer where they are thoroughly blended by the mixer blades 19 to result in a homogenous mass which is discharged from the dispensing opening 21.

When the device is left standing for a prolonged period of time after part of its contents has been dispensed, the mass contained in the mixer will harden so that the mixer becomes useless. When it is desired to re-use the device, the mixer 11 is unscrewed from the opening 14 of the container 10, whereby the separating element 24 is removed from the container opening 14. Due to this turning movement the component string from the compartment 13 existing in the outer annular space 18 is torn and sheared off in the vicinity of the rear end of the peripheral wall 27, while the component string from the compartment 12 existing in the inner space 15 is torn and sheared off in the vicinity of the rear end of the peripheral wall 26. The mixer 11 including the relatively small quantity of largely hardened mass contained therein and the separating element 14, is discarded.

Subsequently, a fresh empty mixer 11 is attached by screwing. During this action, the partition 16 is turned into the annular groove 25 of the separating element 24, whereby any residues of the components are removed from the inner surface of the partition 16 by the inner peripheral wall 26 and from the outer surface of the partition 16 by the outer peripheral wall 27.

When the screwing action is performed until the afore-described complementary conical faces of the peripheral wall 17 and the sleeve 22 abut each other, the first mixer blade 19 will be in a position in which its leading edge 28 lies in a plane (the drawing plane of FIG. 1) that is defined by the axes of the two compartments 12 and 13. This position is important because the component fed from the compartment 13 will fill the annular space 18 not necessarily uniformly but is advanced at maximum pressure in the right-hand portion in FIG. 1 and at minimum pressure in the left-hand portion of the annular space 18. In the mentioned position of the leading edge 28 this non-uniformity of feeding of the component has the same effect on the two partial strings formed by the first mixer blade 19, so that the homogeneity of the final mixed composition is practially not affected.

Because of the afore-described relation between the axial lengths of the peripheral walls 26 and 27 of the separating element 24 and the cross-sectional areas of the opening spaces 15 and 18, and because of the fact that the component strings were previously sheared off at the above-described locations, both component strings, upon renewed advance of the pistons, will reach the mixer 11 simultaneously so that the newly formed mass has the desired mixing ratio even in its foremost portion.

It has been assumed in the above description that the used mixer 11 is left on the device and is replaced just before operation is resumed. Alternatively, it is possible to remove the mixer immediately after use and to close the container opening 14 with the closure plug 29 shown in FIG. 2, which was originally delivered with the device by the company that filled it. The radial and axial dimensions of the closure plug 29 are designed to correspond to those of the mixer 11 and the separating element 24. Like the sleeve 22 of the mixer 11, the plug is also provided with external threads for screwing into the internal threads of the container opening 14. Since the plug, like the separating element 24, prevents mutual carry-over of the two components and since it is driven into the coaxially configured container opening 14 with a turning motion, it may be used repeatedly.

The modification illustrated in FIG. 3 differs from the embodiment of FIG. 1 mainly as to the configuration of the separating element. As shown in FIG. 3, the separating element 24' is a simple sleeve which surrounds the cylindrical partition 16 of the container 10 along the outer surface thereof and carries an outwardly facing annular flange 30 at its lower end. This annular flange 30 serves the purpose of defining the shearing location of the component string issuing from the compartment 13, while the string issuing from the compartment 12 will be sheared off approximately at the upper end of the cylindrical partition 16.

Figure 4:
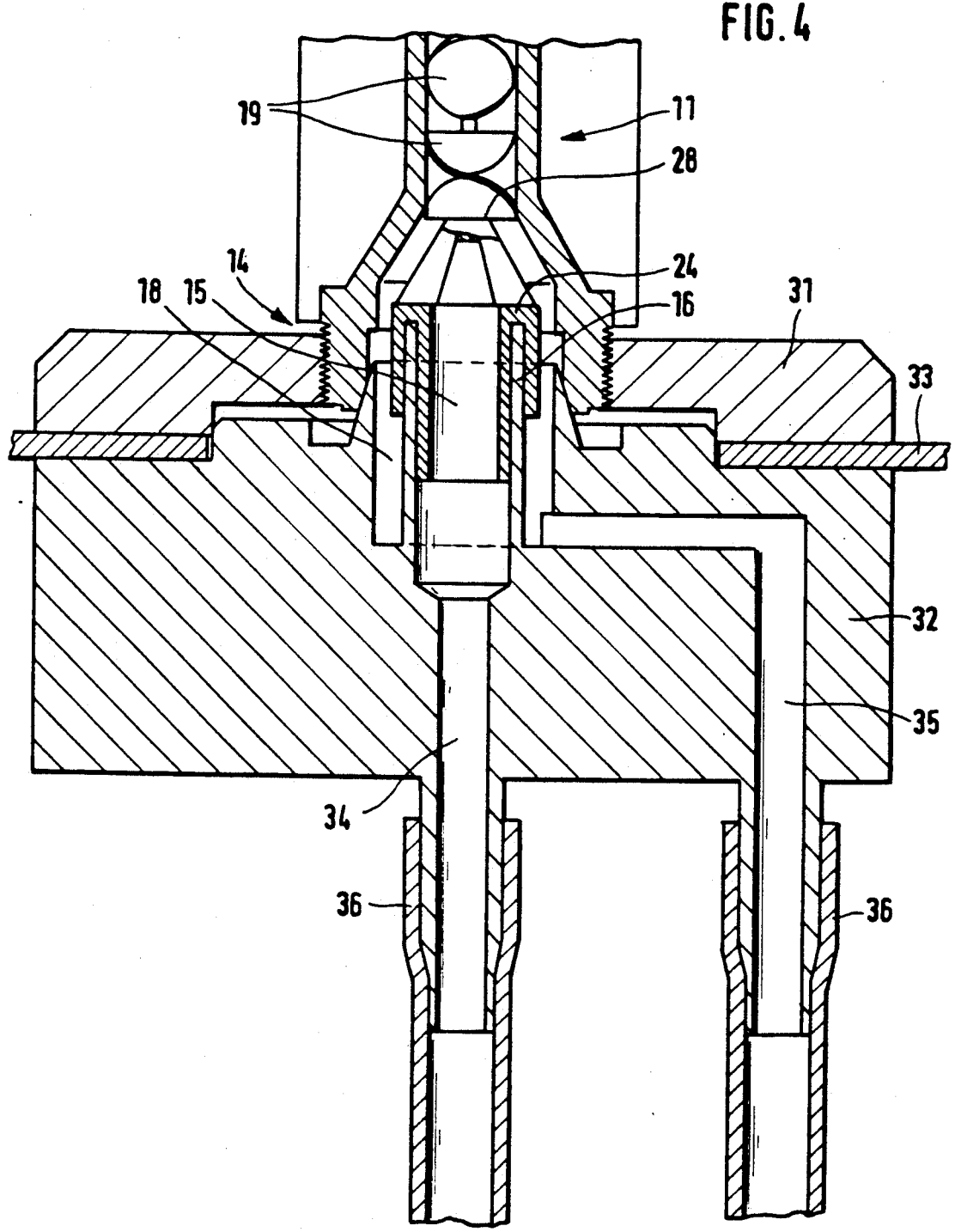

In the embodiment illustrated in FIG. 4, the mixer 11, which may be of a design similar to that shown in FIGS. 1 and 3, is screwed into an opening 14 which is provided in an upper mounting member 31. This upper mounting member 31 as well as a lower mounting member 32 have such configurations and may be assembled in such a way that the device can be mounted in the opening of a working table top 33. The lower member 32 is formed with channels 34, 35 of which one channel 34 opens to the inner space 15 of the opening 14 while the other channel 35 opens to the outer annular space 18 of the opening 14. The cylindrical partition 16 of FIG. 4 is provided in the lower mounting member 32 and serves to separate the inner space 15 from the annular space 18 and to engage the separating element 24 provided on the mixer 11. The channels 34 and 35 communicate via rigid or flexible conduits 36 with reservoirs (not illustrated) from which the components to be mixed are supplied under pressure.

In FIG. 4, the channels 34 and 35 open in the respective spaces 15, 18 of the opening 14 at locations which lie in the drawing plane of FIG. 4. For the reason explained in conjunction with FIG. 1, it is advantageous for the leading edge 28 of the first mixer blade 19 to be disposed in the same plane.

In a further embodiment (not illustrated), the component passing through the annular space 18 of the opening 14 may be supplied through two diametrically opposed channels or even through a plurality of circumferentially distributed channels, so that the annular space 18 will be filled more uniformly. In this case the leading edge 28 of the first mixer blade 19 may take any desired orientation.

We claim:

1. A device for mixing two components which react with each other and for dispensing the pasty mass mixed therefrom, comprising:

a body member having separate feed means for said components, a circular opening having a cylindrical partition dividing said opening into an inner space and an annular outer space, said inner space communicating with one of said feed means, and said outer space communicating with another one of said feed means, a static mixer including a tubular housing having a rear open end adapted for connection to the opening of said body member and a dispensing opening at its forward end, and a sleeve-shaped separating element formed with outer and inner peripheral walls defining a rearwardly open annular groove therebetween which is joined to the rear end of said mixer, said separating element upon fitting of said mixer onto said body member receiving said partition in said annular groove and being sealingly connected to said cylindrical partition to constitute an extension thereof, said separating element serving to separate the two components until they reach said mixer.

2. The device of claim 1, wherein said circular opening of said body member is internally threaded.

3. The device of claim 2, wherein said mixer housing has an externally threaded portion engageable with said threaded member for removably securing said mixer housing to said body member.

4. The device of claim 3, wherein the end face of the externally threaded mixer housing and the end face of said outer peripheral wall of said separating element lie substantially in the same plane.

5. The device of claim 1, wherein the ratio of the lengths of said outer and inner peripheral walls of said separating element is substantially inversely proportional to the ratio of the cross-sectional areas of said outer and inner spaces of said circular opening.

6. The device of claim 1, wherein said feed means are disposed in side-by-side relationship with axes parallel to the dispensing direction, and wherein said mixer includes a series of blades, the leading edge of the first mixer blade lying in the plane defined by said axes.

7. The device of claim 1, wherein said separating element is formed integrally with said mixer.

8. The device of claim 1, wherein said body member is formed as a container having compartments for holding the components to be mixed, said compartments constituting said feed means and being sealed.

9. The device of claim 1, wherein said body member is composed of structural parts adapted to be mounted in a working table, said feed means being formed by supply lines for connection to separate external component reservoirs.

* * * * *